(12) United States Patent
Marx

(10) Patent No.: US 12,115,292 B2
(45) Date of Patent: Oct. 15, 2024

(54) SCENT DISPENSER

(71) Applicant: Michael J. Marx, White Lake, MI (US)

(72) Inventor: Michael J. Marx, White Lake, MI (US)

(*) Notice: Subject to any disclaimer, the term of this patent is extended or adjusted under 35 U.S.C. 154(b) by 569 days.

(21) Appl. No.: 17/536,220

(22) Filed: Nov. 29, 2021

(65) Prior Publication Data

US 2022/0168458 A1 Jun. 2, 2022

Related U.S. Application Data

(60) Provisional application No. 63/119,600, filed on Nov. 30, 2020.

(51) Int. Cl.
| | |
|---|---|
| *A61L 9/12* | (2006.01) |
| *A01M 29/12* | (2011.01) |
| *A61L 9/01* | (2006.01) |
| *B64U 10/00* | (2023.01) |
| *B64U 101/31* | (2023.01) |

(52) U.S. Cl.
CPC .............. *A61L 9/122* (2013.01); *A01M 29/12* (2013.01); *A61L 9/01* (2013.01); *A61L 2209/111* (2013.01); *A61L 2209/12* (2013.01); *A61L 2209/15* (2013.01); *B64U 10/00* (2023.01); *B64U 2101/31* (2023.01); *B64U 2201/20* (2023.01)

(58) Field of Classification Search
CPC .... A61L 9/122; A61L 9/125; A61L 2209/111; A61L 2209/15; A61L 2209/12; A01M 29/12; B64U 2101/31
See application file for complete search history.

(56) References Cited

U.S. PATENT DOCUMENTS 6,443,434 B1 * 9/2002 Prather ..................... A61L 9/03
261/142

* cited by examiner

*Primary Examiner* — Lessanework Seifu
(74) *Attorney, Agent, or Firm* — Harness, Dickey & Pierce, P.L.C.

(57) ABSTRACT

A scent dispenser includes an elongated main body having an outer wall and a fan body slidably engaged with the elongated main body. The fan body has a first retracted position and a first extended position relative to the elongated main body. A fan is disposed within the fan body. A power source is disposed within the fan body and is coupled to the fan. A scent body is slidably engaged with the elongated main body. The scent body has a second retracted position and a second extended position relative to the elongated main body. A scent holder is disposed in the scent body.

26 Claims, 15 Drawing Sheets

SCENT DISPENSER

CROSS-REFERENCE TO RELATED APPLICATION

This application claims the benefit of U.S. Provisional Application No. 63/119,600, filed on Nov. 30, 2020. The entire disclosure of the above applications is incorporated herein by reference.

FIELD

The present disclosure relates to a scent dispenser and, more particularly, to a scent dispenser for attracting and repelling animals.

BACKGROUND

This section provides background information related to the present disclosure which is not necessarily prior art.

Hunters often place bait in a hunting area to attract target animals. For deer, hunters often place carrots, sugar beets or apples in a location in the hopes of attracting a deer to the area. One problem with the use of bait is that more than one deer is often attracted to the area. When deer are diseased, the close proximity of the deer at the bait pile may cause the disease to spread. Many states have outlawed the use of bait to prevent the spread of disease, like chronic waste disease. It has been found that providing a desirable scent without providing food will attract deer but not cause them to congregate. Providing scents in an area is therefore legal.

In residential areas, deer often eat the landscaping plants of homeowners. Providing a repellant for such areas is often times tricky or feudal.

SUMMARY

This section provides a general summary of the disclosure, and is not a comprehensive disclosure of its full scope or all of its features.

The present dispense allows scents to be conveniently provide and dispersed into a wide area. The scents can be an attractant or a repellant depending upon the purpose.

In one aspect of the disclosure, a scent dispenser includes an elongated main body having a outer wall and a fan body slidably engaged with the elongated main body. The fan body has a first retracted position and a first extended position relative to the elongated main body. A fan is disposed within the fan body. A power source is disposed within the fan body and is coupled to the fan. A scent body is slidably engaged with the elongated main body. The scent body has a second retracted position and a second extended position relative to the elongated main body. A scent holder is disposed in the scent body.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
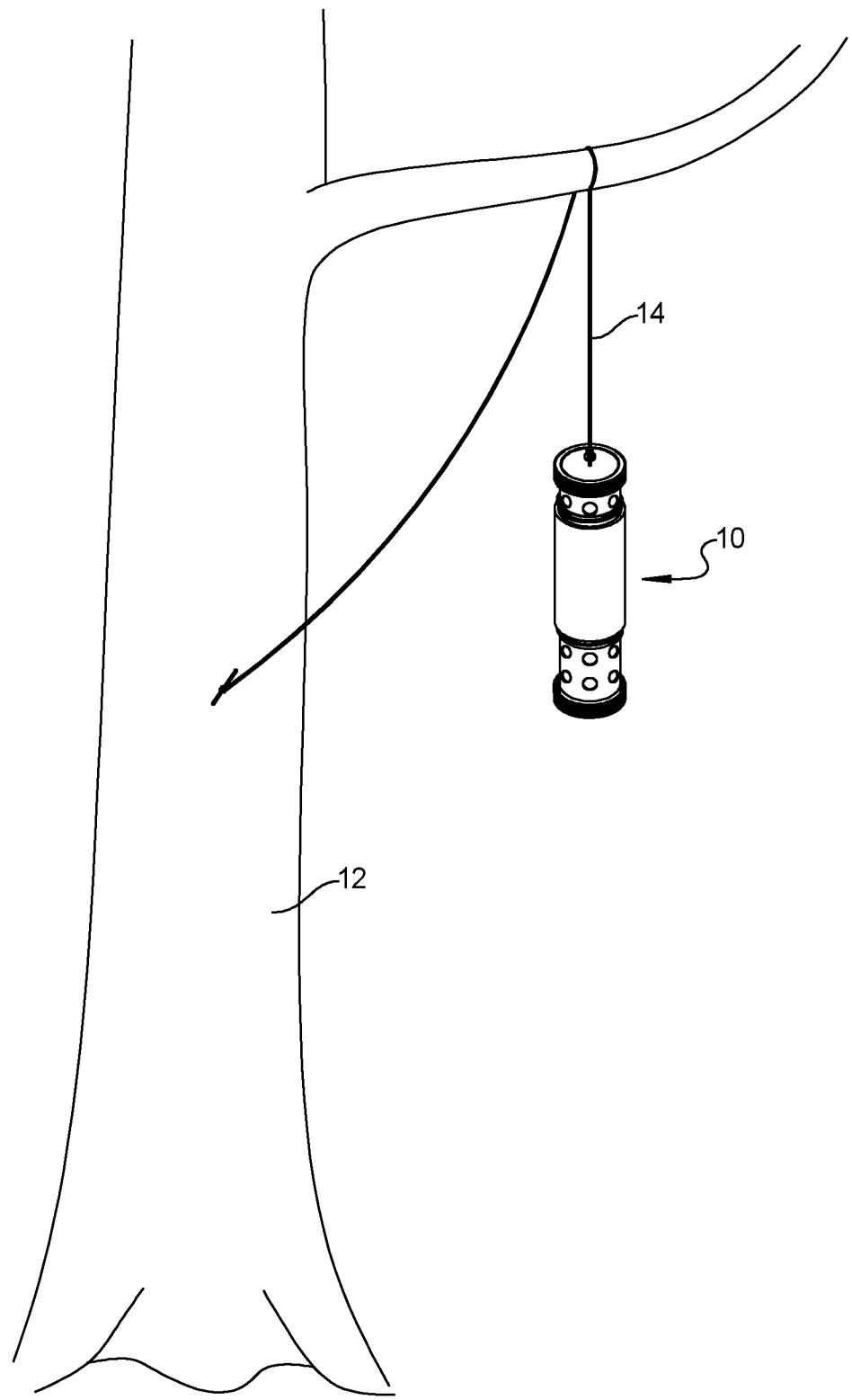
FIG. 1 is a perspective view of a scent dispenser according to the present disclosure.

Referring now to FIG. 1, a scent dispenser 10 is illustrated in use hanging from a tree 12. A rope 14 coupled to the top of the scent dispenser is used to suspend the scent dispenser above the ground. The rope 14 has a first end coupled to the scent dispenser 10 and a second end that is tied around the tree 12. As illustrated, the scent dispenser has an elongated shape in detail below.

Figure 2:
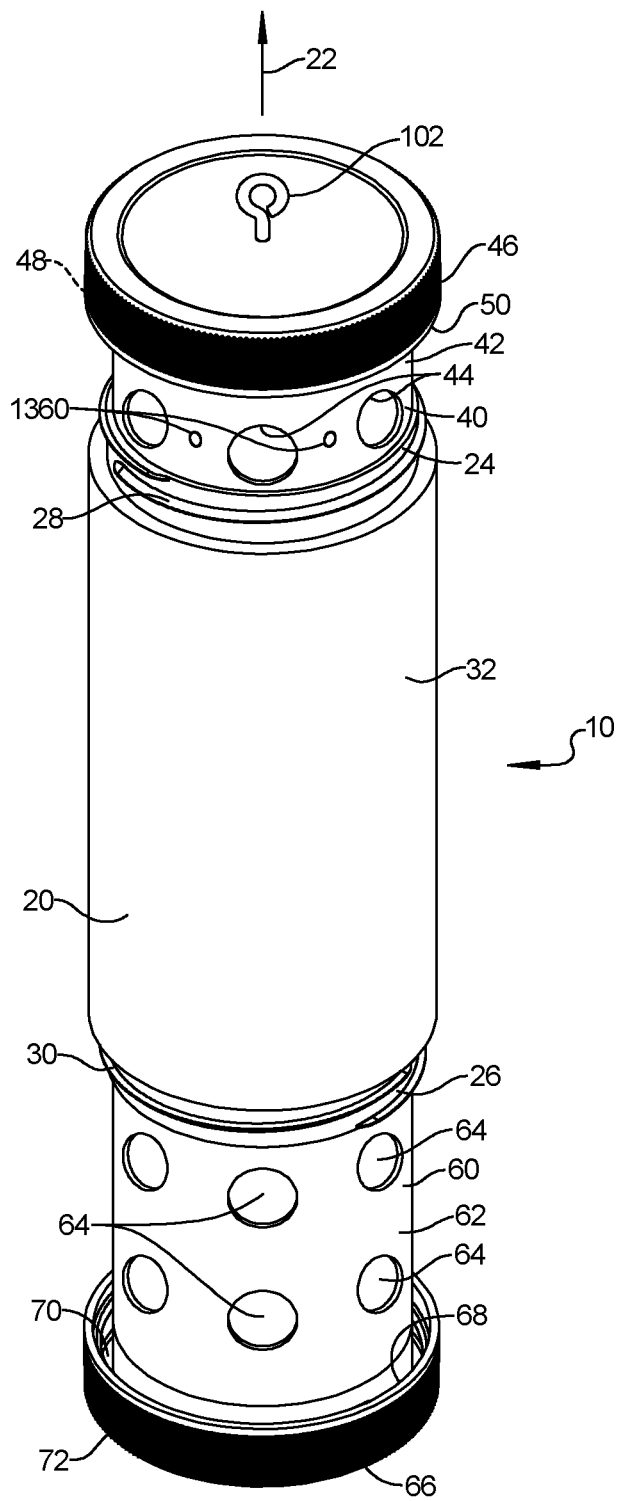
FIG. 2 is a perspective view of the scent dispenser of FIG. 1.
Figure 3:
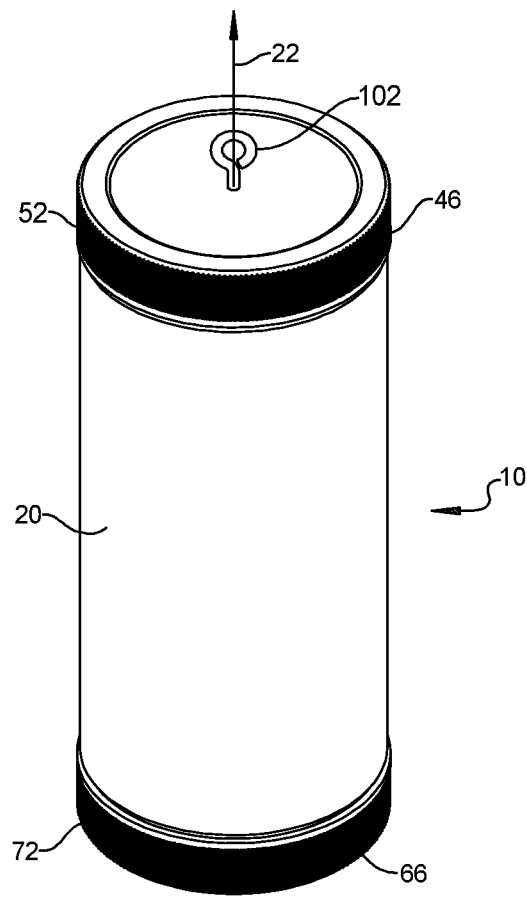
FIG. 3 is a perspective view of the scent dispenser in a retracted position.

Referring now to FIGS. 2 and 3, the scent dispenser 10 is illustrated in an open position and a closed position, respectively. In general, the scent dispenser 10 has an elongated main body 20. In this example, the elongated main body 20 forms an outer housing. The main body 20 is cylindrical in shape and has a longitudinal axis 22. The elongated main body 20 has a first end 24 and a second end 26 opposite the first end 24. The first end 24 and the second end 26 may also be referred to as the upper end and lower end respectively. The upper end and lower end corresponds to when the scent dispenser 10 is in use. The first end 24 has threads 28 disposed thereon. The second end 26 has threads disposed thereon.

The scent dispenser 10 includes an upper inner housing or fan body 40. The fan body 40 is slidably received within the elongated main body 20. The fan body 40 is also cylindrical in shape. The fan body 40 has an outer wall 42 that is sized to have a diameter just smaller than the outer wall 32 of the elongated main body 20.

The fan body 40 also includes a top end cap or top cover 46. The top cover 46 has a diameter greater than the diameter of the outer wall 42. Threads 48 are disposed within the top cover 46 and engage the threads 28 on the first end 24 of the outer wall 32. The top cover 46 is fixedly coupled to the outer wall 42 such that when the fan body and thus the outer wall 42 is slide into the outer wall 32, the threads 48 engage the threads 28.

The top cover 46 forms a channel 50 between a flange 52 and the outer wall 42. That is, the channel 50 is disposed between the flange 52 and the outer wall 42. The inner surface of the flange 52 has the threads 48 disposed thereon.

The scent dispenser 10 also has a lower inner housing or scent body 60. The scent body 60 has an outer wall 62 that is slidably received within the outer wall 32. That is, the outer diameter of the outer wall 62 is slightly less than the inner diameter of the outer wall 32. The outer wall 62 of the scent body 60 has openings 64 therethrough. In this example, two rows of openings 64 are disposed around the circumference of the outer wall 62. The openings 44 allow air to flow into the scent dispenser through the elongated main body, pick up scent and flow scent out the openings 64.

The outer wall 62 has an bottom end cap or bottom cover 66 fixedly attached thereto. The bottom cover 66 has a diameter that is greater than the diameter of the outer wall 62. Threads 68 are disposed within the bottom cover 66 opposite the outer wall 62. That is, the bottom cover 66 forms a channel 70 at a flange 72 of the bottom cover 66. On the inner surface of the flange 72, the threads 68 are formed.

In FIG. 2, the fan body 40 and the scent body 60 are in a fully extended position. In FIG. 3, the fan body 40 and the scent body 60 are in a fully extended position. As will be described in more detail below, the fan body 40 and the scent body 60 engage the main body 20 to retain the components together. In the retracted position, an enclosed retail package is formed when the covers are closed and locked into position using the threads.

Figure 4:
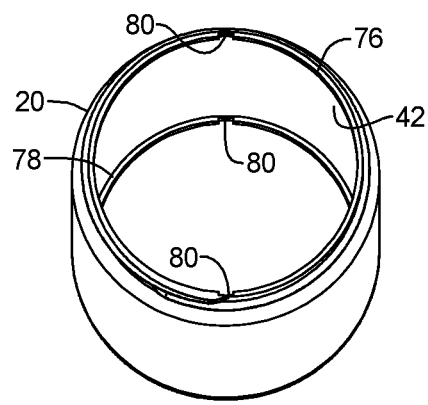
FIG. 4 is an internal perspective view of the elongated body of the scent dispenser.

Referring now to FIG. 4, a perspective view into the elongated main body 20 is provided. The elongated main body 20 includes an upper flange 76 and a lower flange 78. Each flange 76, 78 extends inward from the outer wall 42, a predetermined distance. The flanges 76, 78 form a reduced diameter opening. As will be described in more detail below, the flanges 76, 78 are used to retain the fan body 40 and scent body 60 therein. For assembly and disassembly, notches 80 are formed therein.

Figure 5A:
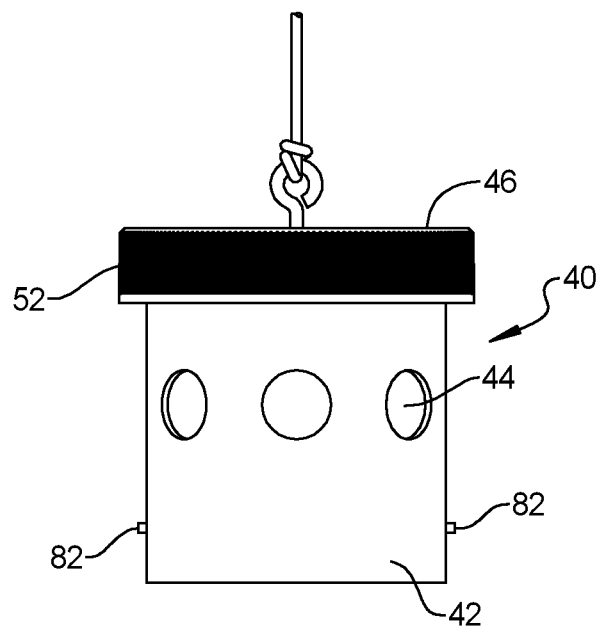
FIG. 5A is a side view of the fan body of the scent dispenser.
Figure 5B:
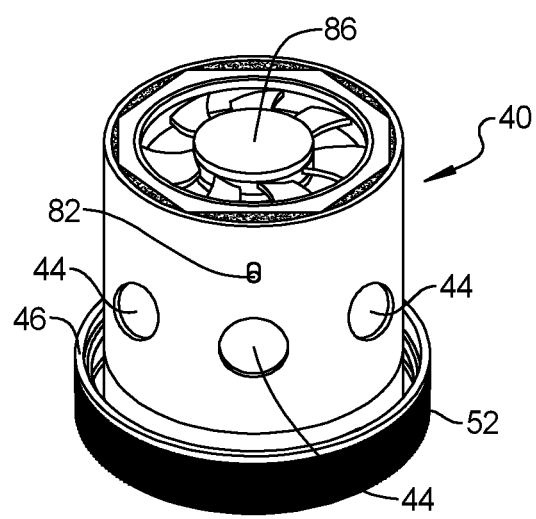
FIG. 5B is an underside perspective view of the fan body of the scent dispenser.

Referring now to FIGS. 5A and 5B, a side view of the fan body 40 is set forth. The fan body 40 has the outer wall 42 as mentioned above. The outer wall 42 has openings 44 that have an engagement member or members 82 extending therefrom. The engagement members 82 may, for example, be a rod that extends across the diameter of the outer wall 42. However, the engagement members may also be integrally formed with the outside of the outer wall 42. The engagement members 82 are sized to be received within the notches 80 in the upper flange 76. Thus, during manufacturing, the engagement members 82 are aligned with the notches 80 in the upper flange and rotated so that the main body 20 is suspended from the engagement members 82 by the upper flange 76 when in use.

Figure 6:
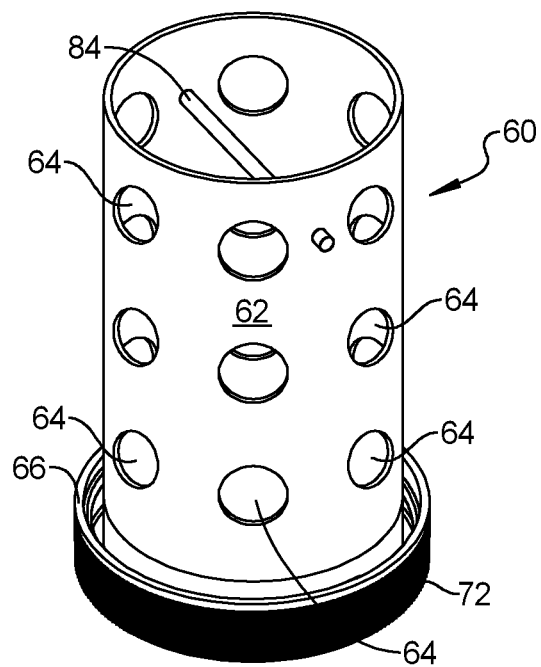
FIG. 6 is a perspective view of the scent body of the scent dispenser.

Referring now to FIG. 6, the scent body 60 is illustrated in further detail. In this example, engagement member or members 84 are used to secure the scent body 60 to the flange 78 illustrated above. The engagement members 84 extend a distance to fit within the notches 80 within the lower flange 78 during assembly. The scent body 60 is rotated around the longitudinal axis to allow the engagement members 84 to engage the upper surface of the lower flange 78 after the engagement members are placed through the notches 80. As mentioned above and similar to that of the engagement members 82, the engagement members 84 may be integrally molded to the outer wall 62 or formed as a separate component such as a rod or the like that extends through the diameter of the outer wall 62. Adhesive glue or the like may be used to position the engagement members 84.

Figure 7:
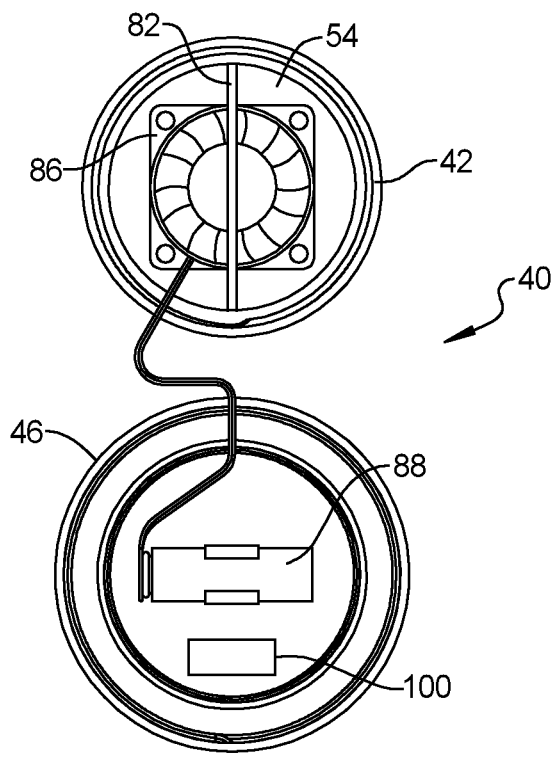
FIG. 7 is an internal view of the fan body opened.

Referring now to FIG. 7, the interior of the fan body 40 is illustrated in further detail. In this example, the top cover 46 has been removed so that the interior is exposed. In this example, the fan body 40 houses a fan 86 and a power source 88. In this example, the power source 88 is a 9 volt battery. Control electronics 100 may also be incorporated into the fan body 40. The control electronics that include a controller and various sensors and interfaces are described in more detail below. In this example, the engagement member 82 extends across the fan body 40.

Figure 8:
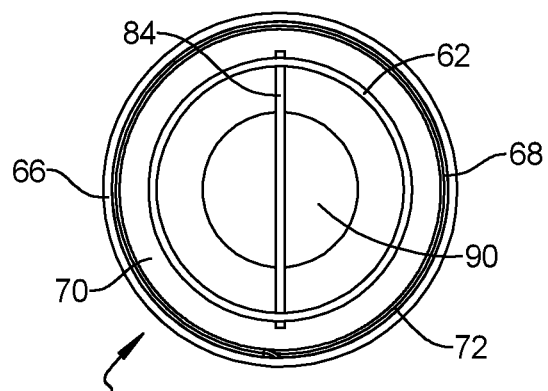
FIG. 8 is an internal view of the scent body.

Referring now to FIG. 8, the interior of the scent body 60 is illustrated in further detail. As shown, the outer wall 62 is generally cylindrically shaped. The inside of the cover 66 is illustrated. A scent holder 90 is illustrated thereon. The scent holder 90 may merely be the top surface of the bottom cover 66. The scent holder 90 may hold a scent wafer or other solid form of dispensing a scent.

Figure 9:
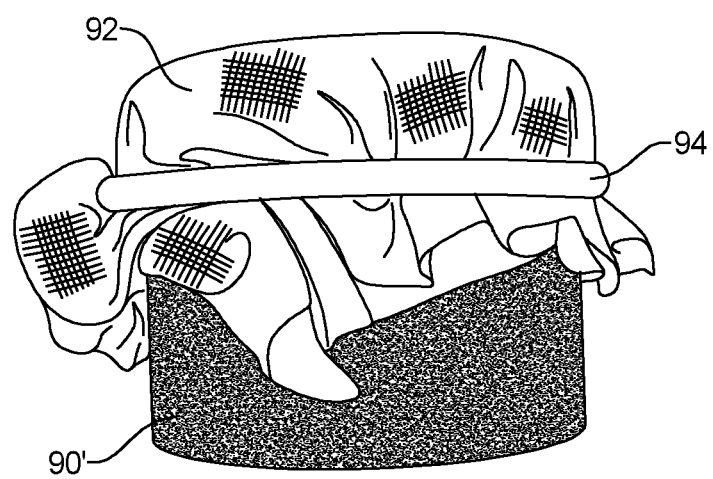
FIG. 9 is a side view of a scent holder.

Referring now to FIG. 9, an alternative scent holder 90' is illustrated. In this example, the scent holder 90' is cup-shaped or cylindrical in shape and has a porous cover 92 disposed thereon. The scent holder may be used for holding a liquid form of scent. The scent holder may be formed of various materials including a wall formed of plastic or glass or other materials. The cover 92 may be fastened to the scent holder 90 with a fastener 94. In this example, the fastener 94 is an elastic band.

Figure 10:
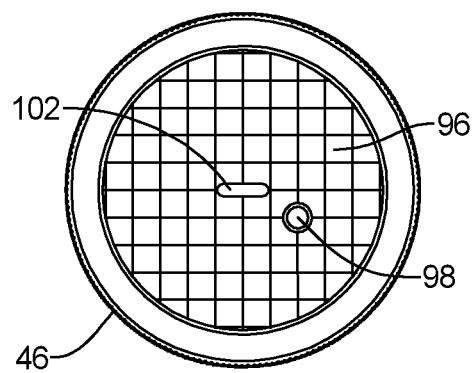
FIG. 10 is a top view of the scent dispenser.

Referring now to FIG. 10, the top cover 46 is illustrated in further detail. The system may include a solar panel 96. The solar panel 96 is fastened to a top surface of the top cover 46. The solar panel 96 may be coupled to the battery 88 for recharging. The solar panel 96 may also be coupled to a charging circuit as will be described in further detail below. A user interface 98 such as a button may also be incorporated into the scent dispenser 10. In this example, the user interface 98 is coupled to the top surface of the top cover 46. The user interface 98 may provide inputs for starting, stopping and performing various functions. Of course, multiple buttons, switches or dials may be incorporated as the user interface 98. In the simplest sense the user interface 98 may be a switch to turn on and off the fan.

A fastener loop 102 may also be coupled to the top cover 46. The fastener loop 102 may be used to secure the rope 14 illustrated in FIG. 1. Of course, other types of fasteners may be incorporated for securing the scent dispenser 10 to various structures.

Figure 11:
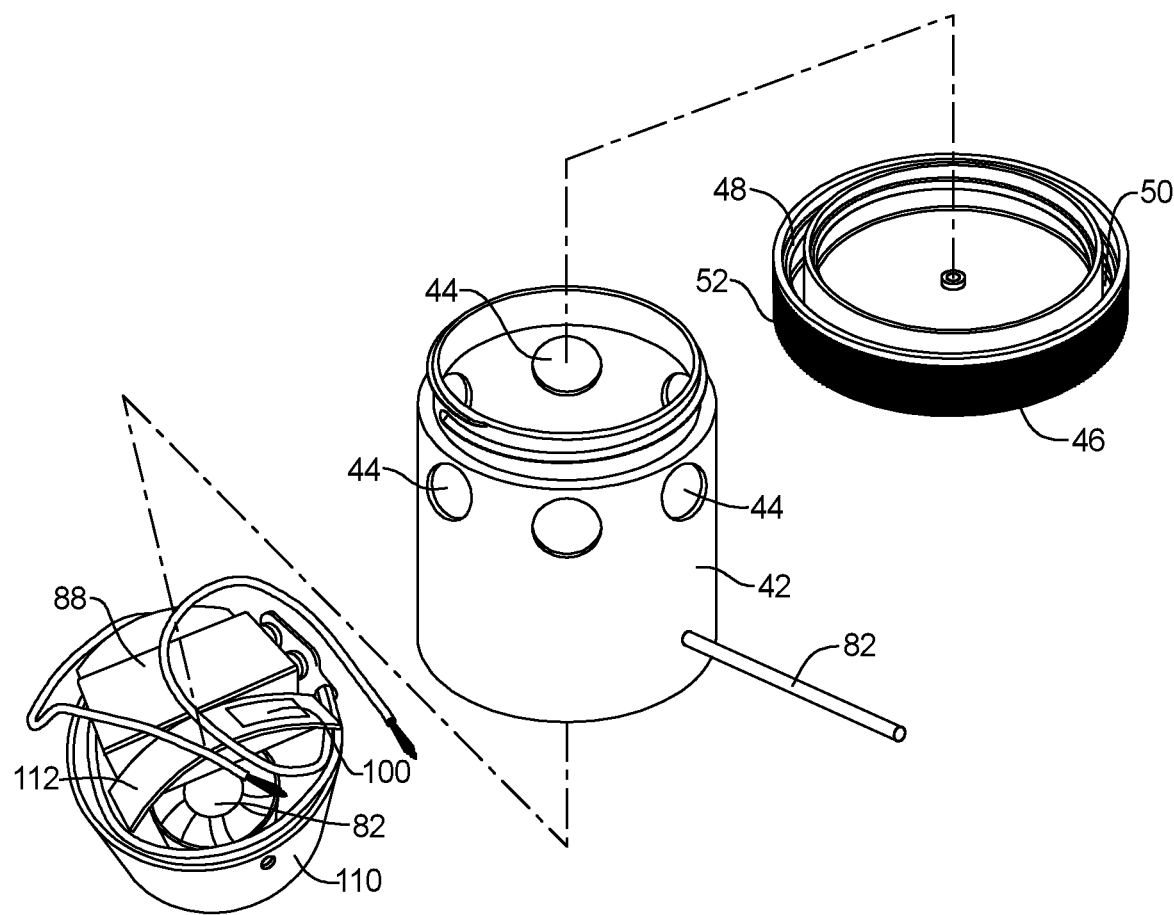
FIG. 11 is an exploded perspective view of an alternate fan body.

Referring now to FIG. 11, an alternate means for securing the fan 86 and the power source 88 is set forth. A fan holder 110 may be secured to the outer wall 42 within the fan body 40. Integrally formed structures may be used for securing the fan holder 110 to the fan body. The fan holder 110 may be cup-shaped. The fan holder 110 may have a support 112 that extends across the fan holder 110 to support the battery 88 and the control electronics 100. The fan holder 110 may be removably coupled to the inner portion of the outer wall 42 by the engagement member 82. In this manner, the battery may be accessed and replaced. That is, the retaining member 82 may be removed (or the fan holder disengages from another type of retainer) and the fan holder 110 removed from within the outer wall 42 so that access to the power source 88, such as the battery, may be achieved. The fan holder 110 may have integrally formed tabs for receiving the battery 88 therein.

Figure 12:
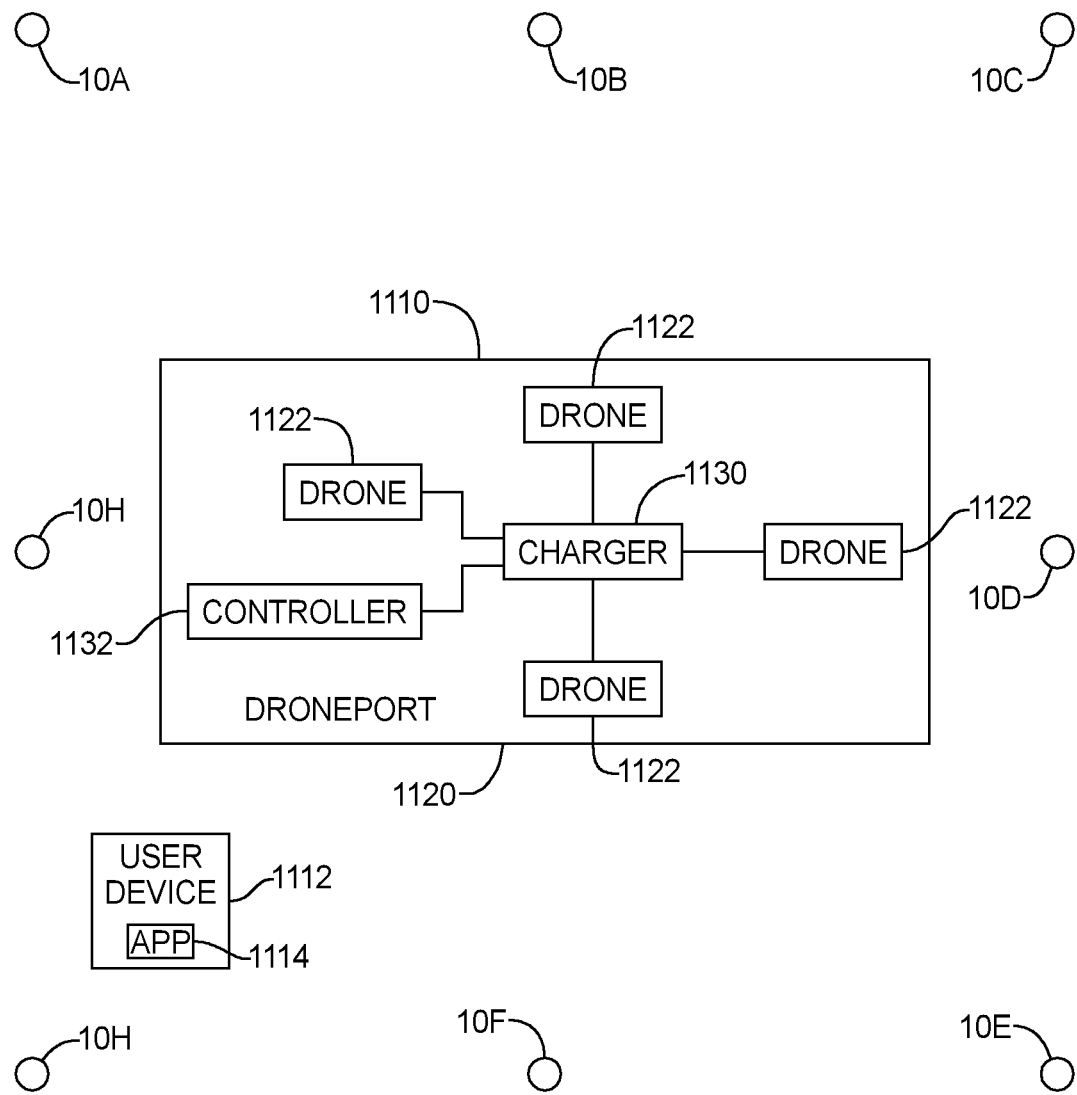
FIG. 12 is a schematic view of a system for controlling a field of interest.

Referring now to FIG. 12 a plurality of scent dispensers 10A-10H are spaced around an area of interest 1110. A user device 1112 is used to program the position of the devices 10A-10H into an application 1114. This may be done by tuning on each device in turn and selecting a user identifier generated from the particular scent dispenser. This may be performed by walking around a field and placing the scent dispenser 10 into a desired location.

A drone port 1120 is at or near the field of interest. The drone port 1120 has one or a plurality of drones associated therewith. Although four drones 1122 are illustrated more or fewer drones 1122. The number of drones 1122 may correspond to the size of the area to be of interest to be monitored.

The drone port 1120 may have a charger 1130 and a controller 1132. The charger 1130 recharges the drones 1122. The controller 1132 may receive commands from the user device and control which drone 1122 is dispatched to a threat.

Figure 13:
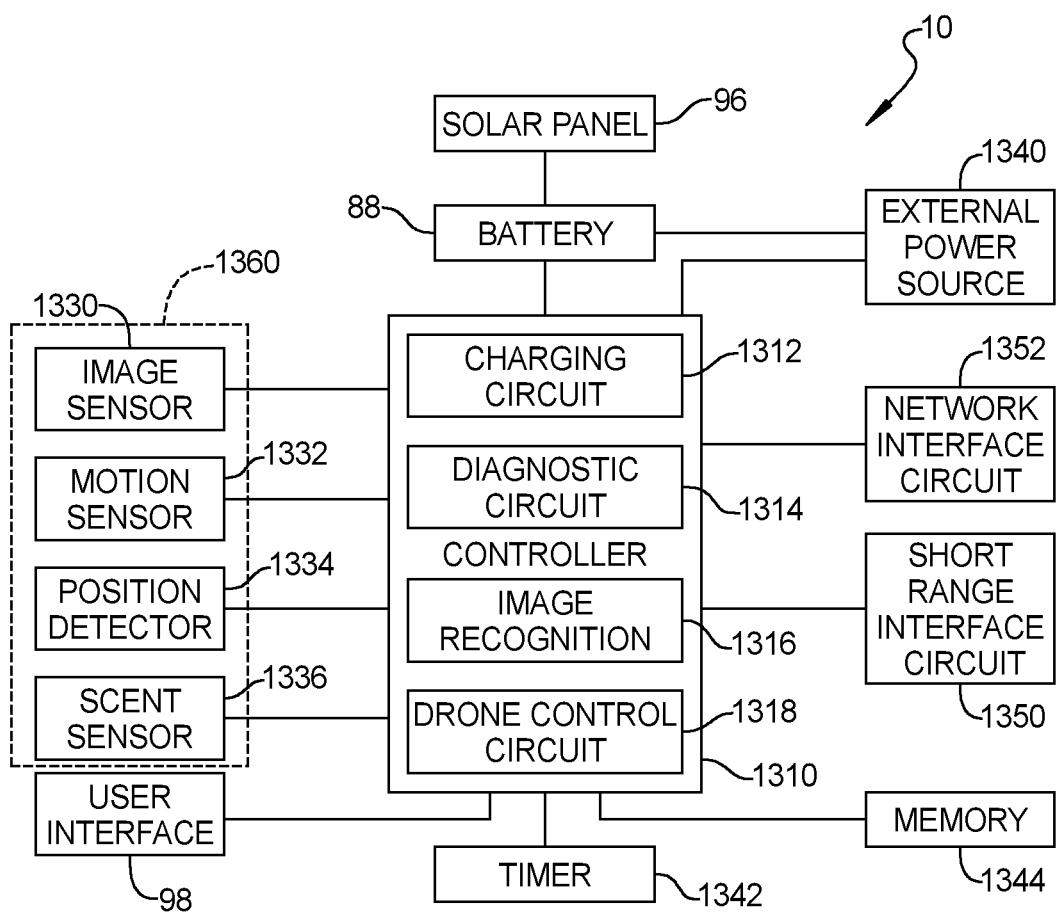
FIG. 13 is a block diagrammatic view of the control circuit of the scent dispenser.

Referring now to FIG. 13, a control system for the scent dispenser 10 is set forth. The control system includes sensors and interfaces for controlling the operation of the scent dispenser 10 and for dispatching to a threat. The scent dispenser 10 includes a controller 1310. The controller 1310 performs various functions that will be described below. For example, a charging circuit 1312 is coupled to the solar panel 96 and battery 88 to allow the battery 88 to sufficiently charge and enable overnight operation. The controller includes a diagnostic circuit 1314 that uses various inputs to determine whether the system is not operating properly.

The controller 1310 also includes image recognition 1316 for determining the present of various types of intruders such as an animal or a person within view of the system. The controller 1310 also includes a drone control circuit 1318. The drone control circuit 1318 controls the release of a drone that is used to frighten, provide images of, and scare away intruders within the certain area.

An image sensor 1330 is coupled to the controller 1310. The image sensor 1330 provides images to the controller 1310 that are used in the image recognition circuit 1316. The image sensor 1330 may be various types of cameras or charged coupled devices. The image sensor 1330 may operate both in daylight and using infrared/thermal detection.

A motion sensor 1332 is coupled to the controller 1310. The motion sensor 1332 may be used to activate various operations performed by the controller 1310. The motion sensor 1322 may, for example, activate the image sensor 1330. The image sensor 1330 may also be activated upon the request of a user through the app of the user device as described below.

The controller 1310 may also be coupled to a position detector 1334. The position detector 1334 may be global positioning system detector that senses the global position of the scent dispenser 10. The position detector 1334 generates a position signal corresponding to the position of the scent dispenser 10.

A scent sensor 1336 may also be disposed within the scent dispenser 10. The scent sensor 1336 may be positioned adjacent to the scent holder 90 to determine whether the scent is still potent or available. The scent dispenser 1336 generates a scent signal that corresponds to the amount of scent within the scent holder 90. The scent sensor 1336 may also be weight activated. That is, the scent sensor 1336 may be a load cell that generates a weight signal that corresponds to the amount of scent at the scent holder 90.

The scent sensor may also be coupled to an external power source 1340. The external power source 1340 may be DC power that is used to charge the battery 88 should a solar panel 96 not be used. The external power source 1340 may also be coupled to the controller 1310. The system may be capable of operating strictly on external power from the external power source 1340 without providing a battery therein.

The controller is coupled to a timer 1342 that is used to timed various events. For example, a delay time after a motion signal is received from the motion detector 1332 may be used to trigger the capture of an image from the image sensor 1330. Other timing issues such as providing a time stamp for the image generated at the image sensor 1330 may also be performed.

A memory 1344 is coupled to the controller 1310. The memory 1344 is used to store various operational data and data from the various sensors 1330-1336. The memory 1344 may be used to store an identifier that identifies the scent dispenser 10. For example, the memory 1344 may have a number of other type of alpha numeric identifier associated with the scent dispenser 10.

The controller may also be coupled to a short range interface circuit 1350 and a network interface circuit 1352. Both the interface circuits 1350, 1352 may perform similar functions. The short range interface 1350 may, for example, be Bluetooth for allowing the scent dispensers in adjacent locations to intercommunicate. A network interface 1352 may be used to couple to an external network to allow the data from the scent dispenser to be communicated to an application used by a user. The network interface 1352 may also be used for the scent dispensers 10 to intercommunicate when used in a system.

The network interface 1352 may, for example, be WiFi or a cellular network interface. Likewise, the network interface circuit 1352 may a global cellular satellite phone. The short range interface circuit 1350 may be a short range radio or Bluetooth.

The diagnostic circuit 1314 may generate a diagnostic signal that is communicated to a user device external to the system. The diagnostic circuit 1314 may, for example, generate a battery charge circuit that provides the state of charge of the battery, a fan current circuit corresponding to the current of the fan or a battery replace signal that indicates the battery 88 should be replaced for the system.

Referring now also to FIG. 2, sensor locations 1360 may be disposed at various places around the scent dispenser 10. In this example, the sensor locations 1360 are between the openings 44 of the outer wall 42. However, locations on the top cover 46, the bottom cover 66, the main body 20 and the outer wall 62 may also be used.

Figure 14:
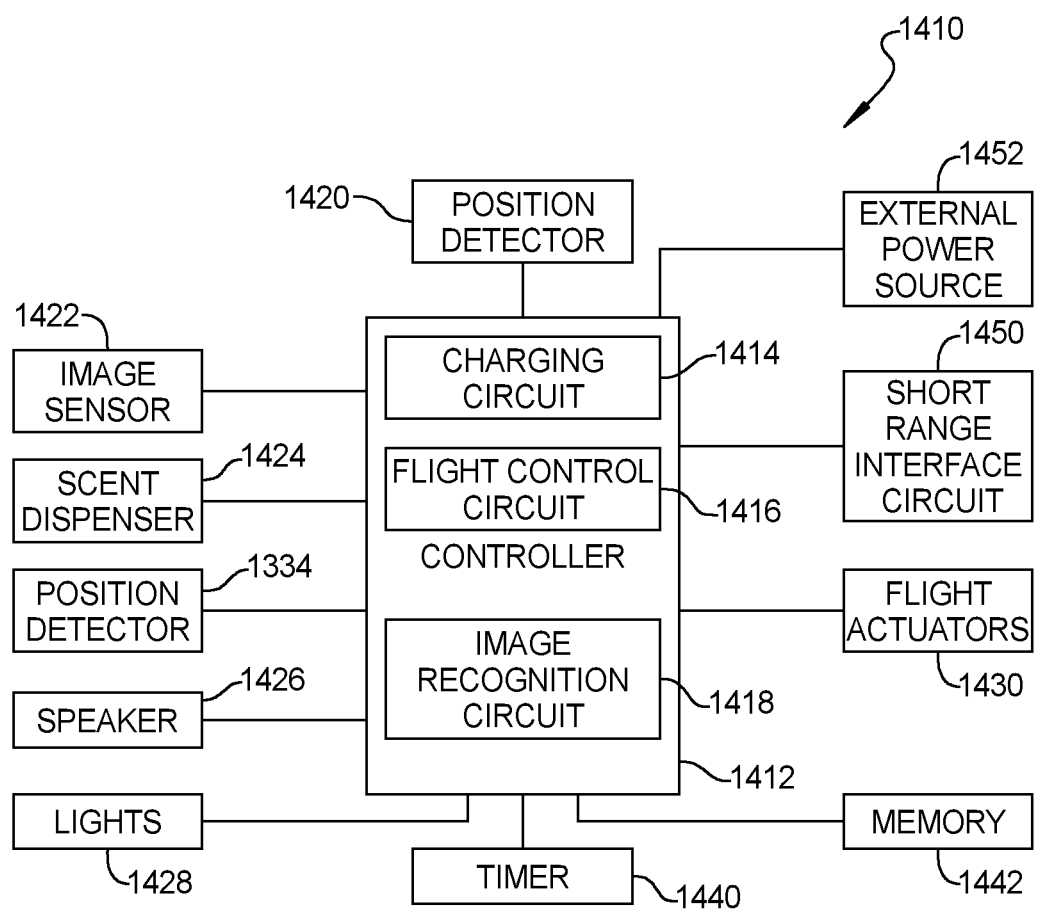
FIG. 14 is a block diagrammatic view of the control circuit of the drone.

Referring now to FIG. 14, a drone control circuit 1410 is illustrated for use in a drone. The drone control circuit 1410 includes a controller 1412 that is microprocessor based and programmed to perform various functions. The controller 1412 may include a charging circuit 1414 and a flight control circuit 1416. The charging circuit 1414 is used for charging and determining when to recharge a power source of the drone. The flight control circuit 1416 is used for controlling the flight to various locations.

A position detector 1420 determines the position of the drone relative to the area to be covered. The position detector 1420 may generate a position signal corresponding to the geographical coordinates of the controller 1412. The position detector 1420 may provide an elevation as well as a latitude and longitude for the drone.

An image sensor 1422 may generate an image corresponding to a field of view of the drone. The image sensor 1422 may be an infrared, thermal or daylight or combination of both type sensors for generating images. The controller 1412 may also include a scent dispenser 1424. The scent dispenser may be used to provide extra scent to a particular area being monitored.

A speaker 1426 may be used to generate noises to scare away an intruder. Both the scent dispenser and the speaker 1426 may generate scents or sounds to scare away an intruder. In addition, lights 1428 may be used to scare away intruders under the control of the controller 1412. The controller 1412 has an image recognition circuit 1418 for recognizing intruders such as animals or people. The controller 1412 may thus control the flight control circuit 1416 and thus the flight of the flight actuators 1430 based on the scent conditions and the recognized images.

The controller 1412 also includes a timer 1440 used for timing various functions and a memory 1442 used for storing various data during the flight control process. Both the timer 1440 and the memory 1442 operate in a similar manner to those described above in the controller 1310.

A short range interface circuit 1450 and a network interface 1452 may also be coupled to the controller 1412. The short range interface circuit may be a Bluetooth circuit or other short range radial circuit. The network interface circuit 1452 may provide WiFi or cellular network interface. The short range interface circuit 1450 and the network interface circuit 1452 may be used to communicate various scent dispensers within an area being monitored. Likewise, the short range interface circuit 1450 and the network interface circuit 1452 may be used to communicate with a user device located in another location.

Figure 15A:
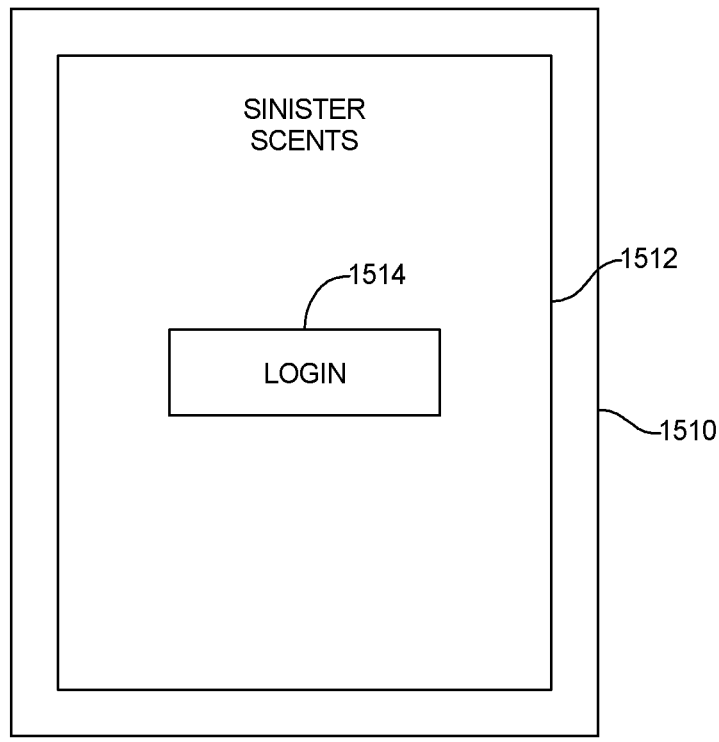
FIG. 15A is a screen display of the login screen.

Referring now to FIG. 15A, a user device 1510 is illustrated having a screen display 1512. The screen display in this example provides a login button 1514 that may be selected to initiate the login process. The login process may require the user to provide various identifying information to use the system.

Figure 15B:
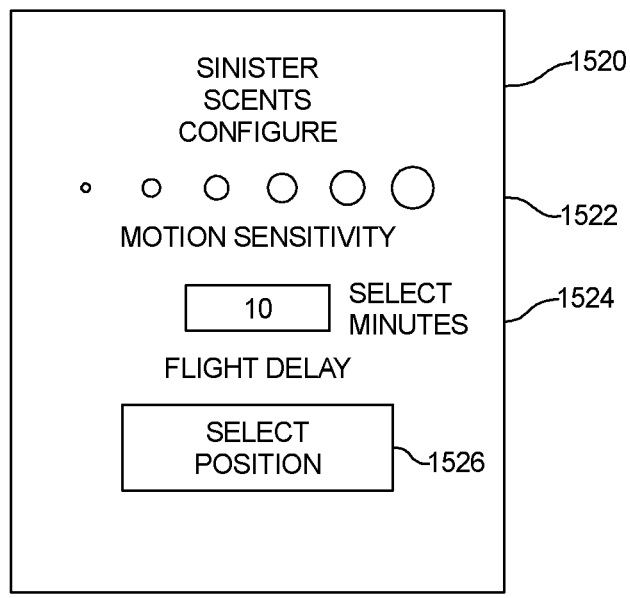
FIG. 15B is a screen display of a control setting.

Referring now to FIG. 15B, the configuration process screen display 1520 is illustrated. In the screen display 1520, a motion sensitivity selector 1522 may be used to select the sensitivity of the motion for a particular scent dispenser. A flight delay selector 1524 may be used to select the delay of launching a drone in response to detection of motion. The flight delay selector 1524 may be used to select the delay of flight from a recognition of an image. A position selector 1526 may initiate the scent dispenser 10 to communicate an identifier to establish its position relative to the field of interest.

Figure 15C:
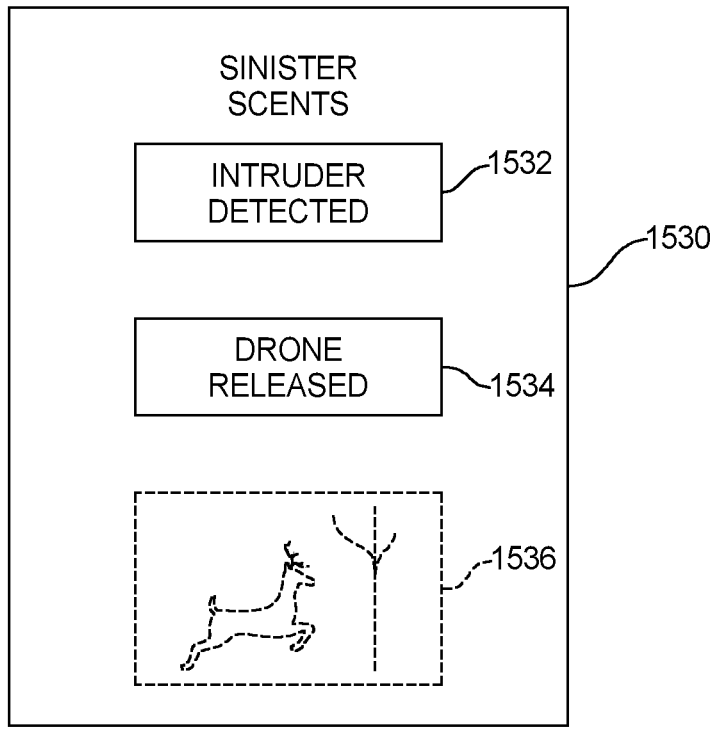
FIG. 15C is a screen display of a detection screen.

Referring now to FIG. 15C, a screen display 1530 may be used to provide various data to a user. In this example, an intruder detected indicator 1532 may be provided to the user. A drone released indicator 1534 may be used to indicate that a drone has been detected. The screen display 1530 may also be used to generate an image 1536 sensed by one of the scent dispensers. The image 1536 may be the image used to activate the release of the drone or the detection of an intruder.

Figure 15D:
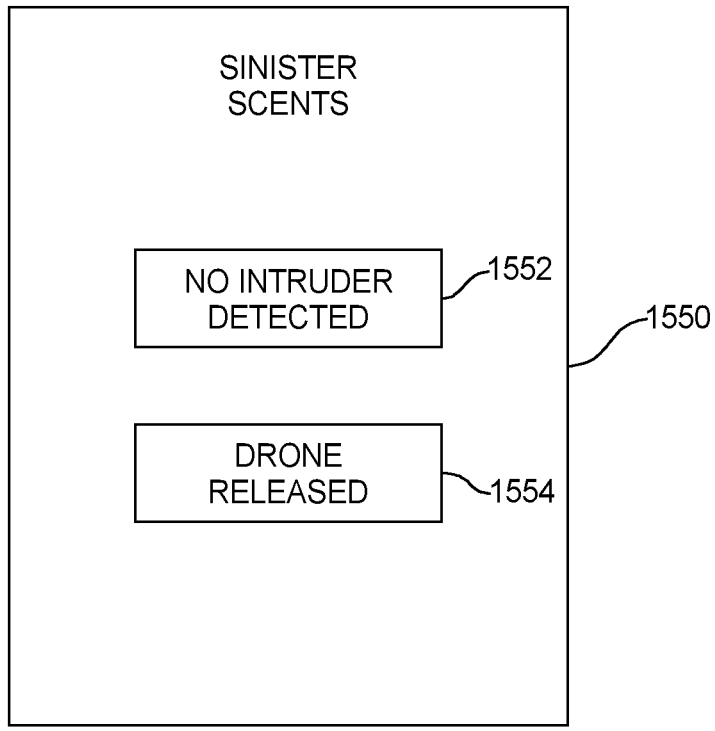
FIG. 15D is a screen display of an operation screen of the application.

Referring now to FIG. 15D, a screen display 1550 for displaying various data is set forth. In this example, a no intruder detected indicator 1552 and a view camera image selector 1554 are displayed on the screen display 1550.

Figure 16:
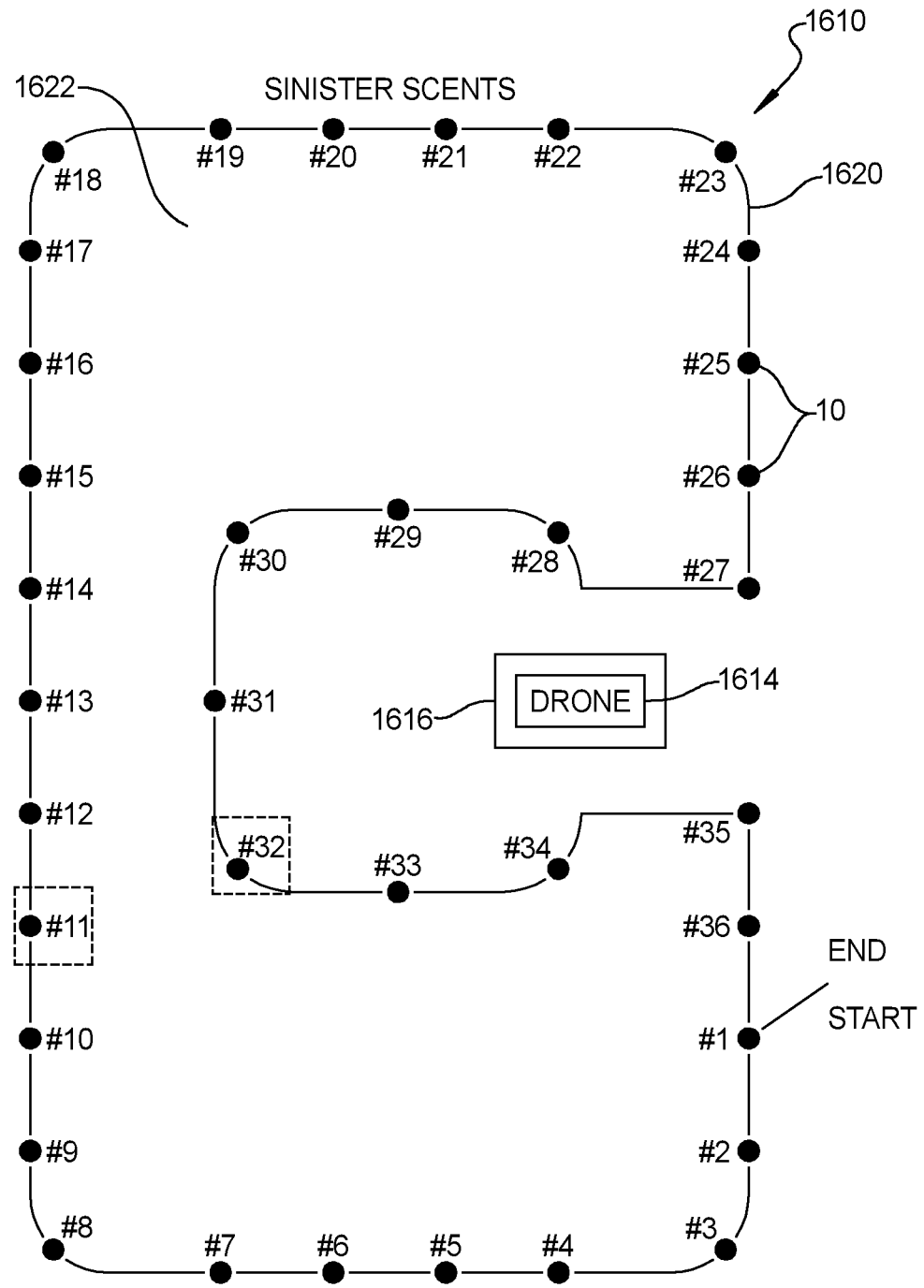
FIG. 16 is a screen display of an area to be monitored together with a position of the drone.

Referring now to FIG. 16, an area of interest 1620 is displayed. In this example, thirty-six scent dispensers 10 are provided. A drone 1614 is illustrated from a drone launching pad 1616. The drone launching pad 1616 may also be used for charging the drone. The image illustrated in FIG. 1610 may also be generated within the app. In this example, the dash lines at scent dispenser 11 and scent dispenser 32 indicate faulty scent dispensers that need attention. In the app, the numbers 32 and 11 may be a different color, such as red, while the remaining scent dispensers may be displayed as green indicating that there is no faults. Each of the scent dispensers may communicate with an adjacent scent dispenser or to a number of closely adjacent scent dispensers. This is controlled through the controller of each of the scent dispensers. The scent dispensers form a perimeter 1620 that defines an area to be monitored 1622. When an image or motion is detected around one of the scent dispensers 10, the drone 1614 may be deployed and scare tactics may be employed to frighten intruders. Further, the drones 1614 may be launched periodically to monitor and access the perimeter and the area to be monitored 1622.

In operation, the user through the screen display at the app may program the various scent dispensers to be used in a system. The sensitivity and other data for deploying the drone and activating the sensitivity is provided through the user interface 98 illustrated in FIG. 13. By providing repellant within the scent dispenser 10, various animals, such as deer, will be repelled and thus the farmer will have increased yield for the crops.

Figure 17:
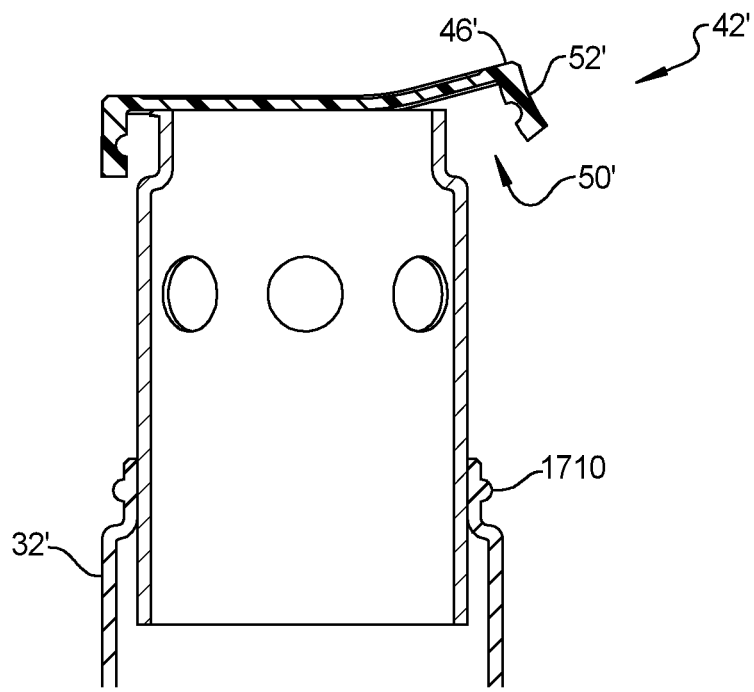
FIG. 17 is a side cross-sectional view of another example of a top cap that is flexible.

Referring now to FIG. 17, an alternate top cover 46 is illustrated. In this example, a flange 52' is illustrated coupled to the outer wall 42. The top cover 46' may be formed of a flexible material such as rubber. The flexible material may be fixedly attached to the wall 42. The flange 52' forms a channel that is disposed between the flange 52' and the outer wall 42. In FIG. 17, the upper housing 42' is shown in an extended position. In the retracted position, the channel 50' and the flange 52' flex to allow the inner portion of the flange 52' to engage the ring 1710 that extends around the outer wall 32'.

Figure 18:
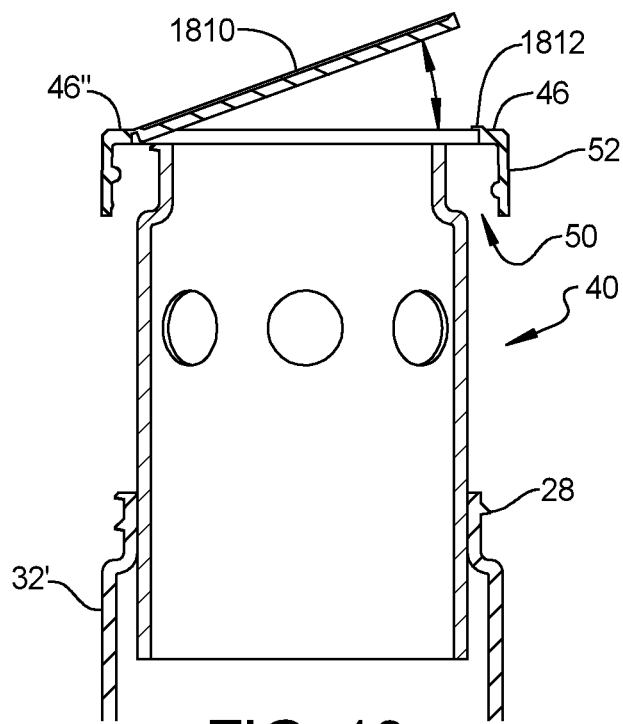
FIG. 18 is a side cross-sectional view of a third example of a top cap with a door.

Referring now to FIG. 18, the flange 52 forms the channel 50 as described above. However, in this example, the top cover 46" has a door 1810 that is held in place by a retainer 1812. The retainer 1812 may be a slide lock or threaded lock to hold the door 1810 closed when in use. The door 1810 allows access within the fan body 40 to change a battery or the like.

In FIGS. 17 and 18, the bottom cover may be formed in the same way as the top covers (i.e., with flexible material or a door). Different top covers and bottom covers may be used in other examples. That is, the type of top covers and bottom covers from the examples above do not have to be the same.

Figure 19A:
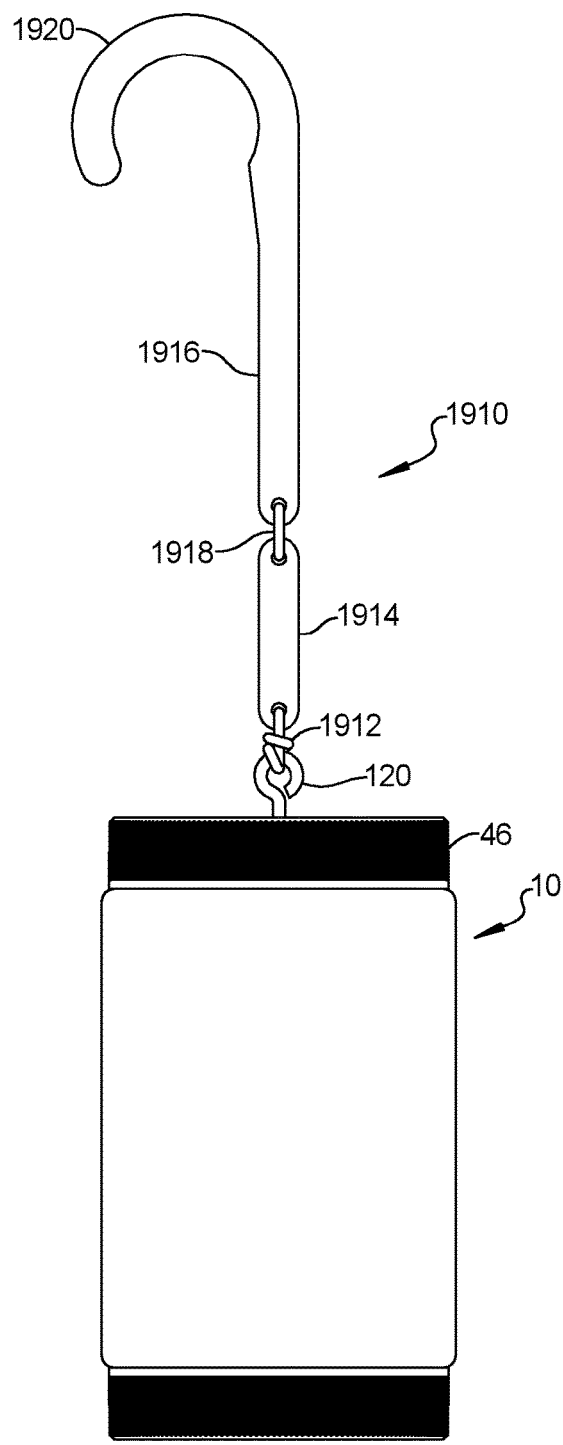
FIG. 19A is a side perspective view of a hanger coupled to a scent dispenser.
Figure 19B:
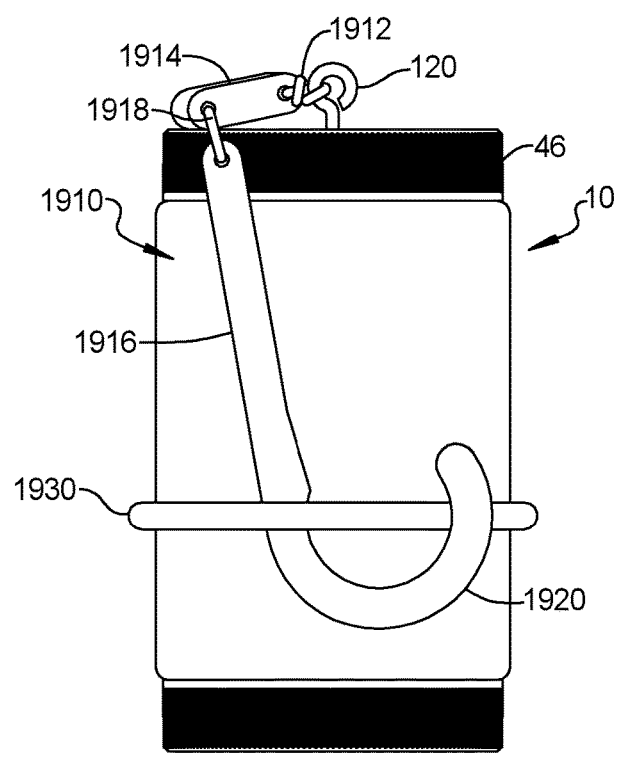
FIG. 19B is a side perspective view of the hanger of the scent dispenser of FIG. 19A in a folded position.

Referring now to FIGS. 19A and 19B, the fastener loop 102 or top cover 46 of the fan body may have a segmented hook 1910 coupled thereto. A flexible coupling 1912 such as wire, string or elastic may be used to couple the segmented hook 1910 to the scent dispenser 10. The segmented hook 1910 comprises a first segment 1914 and a second segment 1916. The first segment 1914 and the second segment 1916 may be coupled together with a second flexible coupling 1918, which may be formed of a similar material as the first flexible coupling 1912. The second segment 1916 of the segmented hook 1910 comprises a hook portion 1920 used for coupling to a tree limb or another attachment location. Because the use is outdoors weather resistant or weatherproof materials may be used for the various components including but not limited to components 1910-1920. A securing device such as a band 1930 may be used securing the second segment to the scent dispenser 10.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A scent dispenser comprising:
   an elongated main body having an outer wall;
   a fan body slidably engaged with the elongated main body, said fan body having a first retracted position and a first extended position relative to the elongated main body;
   a fan disposed within the fan body;
   a power source disposed within the fan body and coupled to the fan;
   a scent body slidably engaged with the elongated main body, said scent body having a second retracted position and a second extended position relative to the elongated main body; and
   a scent holder disposed in the scent body.

2. The scent dispenser of claim 1 wherein the elongated main body, the fan body and the scent body are cylindrically shaped.

3. The scent dispenser of claim 1 wherein the fan body comprises a fan holder and the fan coupled to the fan holder.

4. The scent dispenser of claim 3 wherein the fan holder is removably attached within the fan body.

5. The scent dispenser of claim 1 wherein the power source comprises a battery.

6. The scent dispenser of claim 5 wherein the power source further comprises a solar panel.

7. The scent dispenser of claim 6 wherein the solar panel is coupled to an end cap.

8. The scent dispenser of claim 1 wherein the fan body comprises a first opening therethrough.

9. The scent dispenser of claim 8 wherein the first opening is covered by the elongated main body in the first retracted position.

10. The scent dispenser of claim 9 wherein the scent holder comprises a second opening therethrough.

11. The scent dispenser of claim 10 wherein the second opening is covered by the elongated main body in the second retracted position.

12. The scent dispenser of claim 1 wherein the elongated main body comprises first threads engaging second threads disposed on the fan body.

13. The scent dispenser of claim 12 wherein the elongated main body comprise third threads engaging fourth threads on the scent body.

14. The scent dispenser of claim 13 wherein the first threads and the third threads are disposed on opposite ends of the elongated main body.

15. The scent dispenser of claim 14 wherein the second threads are disposed on a first cover of the fan body.

16. The scent dispenser of claim 15 wherein the fourth threads are disposed in a second cover of the scent body.

17. The scent dispenser of claim 1 wherein the scent holder is cup-shaped.

18. The scent dispenser of claim 1 wherein the scent holder holds a scent wafer.

19. The scent dispenser of claim 1 wherein the scent holder comprises a repellant.

20. The scent dispenser of claim 1 wherein the scent holder comprises an attractant.

21. The scent dispenser of claim 1 further comprising a controller coupled to an interface circuit and an image sensor generating an image signal, said controller programmed to communicate an image to a user device from the scent dispenser.

22. The scent dispenser of claim 21 wherein the controller controlling a drone in response to the image signal.

23. The scent dispenser of claim 22 wherein the drone activates at least one of lights, a drone scent dispenser and sound based controlling.

24. The scent dispenser of claim 21 further comprising a position detector generating a position signal at the scent dispenser and the drone controlling flight in response to the position signal.

25. The scent dispenser of claim 1 wherein the fan body comprises fan body comprising a top cover, said top cover coupled to a segmented hook.

26. The scent dispenser of claim 25 wherein the segmented hook comprises a first segment coupled to the top cover with a first flexible coupling and a second segment coupled to the first segment with a second flexible coupling, said second segment comprising a hook portion.

* * * * *